United States Patent [19]
Perfect

[11] 3,963,120
[45] June 15, 1976

[54] CONTAINER FOR DENTAL MATERIALS AND THE LIKE

[75] Inventor: Alan J. Perfect, Allentown, N.J.

[73] Assignee: Johnson & Johnson, New Brunswick, N.J.

[22] Filed: Feb. 7, 1975

[21] Appl. No.: 548,119

[52] U.S. Cl. .............................. 206/219; 215/314; 220/253; 220/366; 220/377
[51] Int. Cl.² .................. B65D 51/16; B65D 51/18;
[58] Field of Search ............ 128/272; 206/219–220; 215/227, 307, 314; 222/129, 145 220/208; 253; 256; 288; 20.5; 366–367; 220/377; DIG. 27

[56] References Cited
UNITED STATES PATENTS

| | | | |
|---|---|---|---|
| 2,121,554 | 6/1938 | Thorn | 220/253 X |
| 2,527,991 | 10/1950 | Greenburg | 206/220 |
| 3,139,180 | 6/1964 | Kobernick | 206/220 |
| 3,762,540 | 10/1973 | Baumann et al. | 206/219 |
| 3,831,742 | 8/1974 | Gardella et al. | 206/219 |

*Primary Examiner*—Steven E. Lipman

[57] ABSTRACT

A container for prepackaging materials, as for example silver alloy and mercury for dental amalgam, which must be kept separate until just prior to combination and use is disclosed which comprises two chambers. During storage of the materials, the two chambers are separated by a barrier to prevent mixing of the ingredients therein. Combination of the ingredients is effected by twisting the top portion of the container to align a conduit therein with an opening in the barrier between the two chambers. After the material in the upper chamber flows into the lower chamber, the top portion is twisted back to close off the opening and the materials are mixed together by agitating the container.

11 Claims, 9 Drawing Figures

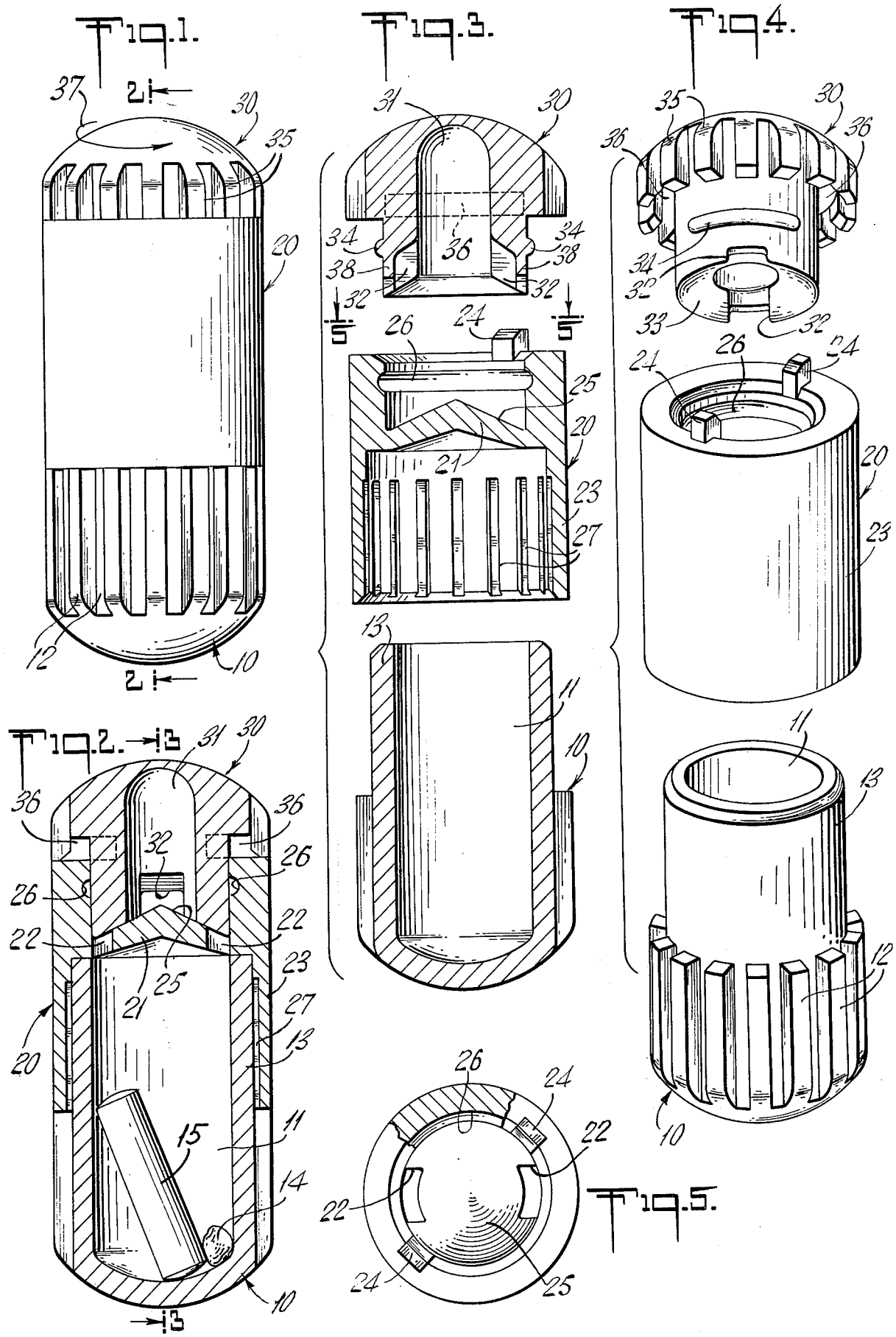

CONTAINER FOR DENTAL MATERIALS AND THE LIKE

BACKGROUND OF THE INVENTION

This invention relates to disposable mixing containers for separate prepackaging of ingredients such as mercury and silver alloy. These ingredients are stored in separate chambers of the container and may be combined and mixed just prior to use.

Dental amalgam of silver alloy and mercury must be prepared just prior to use in a precise formulation. These twin requirements have in the past imposed difficulties upon dental surgeons, who were forced to compound the amalgam themselves, a time-consuming and hazardous task because of the difficulties and dangers inherent in the manipulation of mercury. The accurate measurement of mercury also requires expensive equipment, thus imposing an economic burden on the individual dental surgeon who prepared his own silver amalgam. Their problems have lead to the development of various disposable containers for prepackaging measured amounts of mercury and silver alloy so that they may be mixed just prior to use without the necessity of any measurement or manipulation thereof by the user. These disposable containers also provide more accurate measurement of mercury and silver alloy than would be possible for the individual user because the large volume of production justifies the use of very precise measuring devices, which devices would be uneconomical for the individual dental surgeon.

These prior art containers generally comprise two chambers and a valve means or constricted opening therebetween closed by a valve closing means or occlusion; each ingredient is isolated in its respective chamber. Mixing is generally effected by movement of the occluding portion along the long axis of the container ("translational") with respect to the opening, thus removing the occlusion and allowing communication between the two chambers. The mercury in the upper chamber is allowed to flow into the lower chamber, the occlusion is replaced, and the ingredients are mixed together by agitating the container in an amalgamator or the like as is well known in the art. Examples of these so-called translational containers are disclosed in *Kobernick*, U.S. Pat. Nos. 3,139,180; 3,139,181; and 3,357,545.

These translational containers, while providing for the separate storage of accurately premeasured ingredients, are subject to several disadvantages.

First, the translational nature of the removal of the barrier between the two chambers allows droplets of mercury to be retained on the wall of its chamber and thus not be mixed with the silver alloy. This effect is increased because the occluding portion tends to divide the mercury into several discrete portions during storage. Because of the necessity of accurate compounding of the amalgam to effect the desired properties, such incomplete mixing is highly deleterious.

Second, the translational removal is generally effected by either an unscrewing action or a pulling action on a portion of the container. The unscrewing action is both time-consuming and uncertain, in that the user has no physical indication as to the necessary amount of twisting to effect removal of the occlusion. The pulling action is no better, however, both because of the large amount of friction which hinders the pulling and also because of the possibility of completely separating the pulled portion from the rest of the container with concomitant contamination and loss of materials.

Third, the design of these containers creates manufacturing difficulties. Because of the screw mechanism involved in some types, tolerances must be close if effective segregation of the two chambers is to result.

A further disadvantage in prior art capsules concerns the manner in which the lower, silver alloy containing chamber is formed, generally by sliding the open end of a lower cylindrical portion into the open end of the upper, mercury-containing assembly, the two being held together by friction. But when these two are slid together, the air within is strongly compressed by a sort of piston effect. This trapped compressed air may, upon later heating of the capsule during storage, cause the capsule parts to accidentally disassemble, with concomitant loss or mixing of mercury and silver. Such disassembly, in even small quantities of capsules, is highly undesirable.

These difficulties are obviated by the container of the present invention.

SUMMARY OF THE INVENTION

In accordance with the present invention, there is provided a container for separately prepackaging ingredients such as silver alloy and mercury for later combination and mixing which comprises two chambers. Combination of the ingredients is effected by twisting or rotating the top mercury-containing portion through about 90° with respect to the lower silver-containing portion so as to align a conduit in the top portion with an opening in the barrier between the two chambers. The mercury in the upper chamber then flows through this conduit to combine with the silver, after which the opening is closed by reversing the above opening procedure and the ingredients are mixed to form the amalgam by agitating the container in an amalgamator or like mechanical device as is well known in the art.

This rotational means for effecting a passage from the upper mercury-containing chamber to the lower silver-containing chamber removes the disadvantages inherent in the prior art translational means.

First, the wiping action of the conduit wall over the barrier between the chambers during the twisting step sweeps up any mercury droplets that would otherwise tend to adhere to the upper surface of the barrier. This action provides a more complete and precise transfer of the mercury from its chamber into the silver-containing chamber for mixing than heretofore known, thereby promoting more accurate compounding of amalgam than possible with prior art translational containers. Furthermore, because the container of the invention has no occluding means in the center of the mercury-containing chamber, the mercury tends to remain in a single unit, which also promotes complete transfer thereof into the silver alloy-containing chamber.

Second, the fact that combination of the ingredients is effected by rotational juxtaposition of the conduit and the opening in the barrier, rather than by translational movement of an occlusion out of the opening, allows the user more precise knowledge as to when effective communication between the two chambers is attained. In prior art devices employing a screwing action one could unscrew the upper portion through 360° or more and still not be certain that complete combination of the mercury with the silver alloy had taken place. In those employing a pulling action, on the other hand, the large amount of frictional resistance to the pulling made it uncertain whether complete removal of the occlusion had occurred. These uncertain and time-consuming procedures are avoided in the container of the present invention because a twisting of only about 90° effects complete communication between the two chambers. Achievement of juxtaposition of the conduit and the opening in the barrier is preferably indicated by an arrow or a stop means on the container to prevent twisting beyond the point of juxtaposition.

Third, the design of the container of the present invention, which requires no screwing to function, simplifies the manufacture thereof. Because no screw threads need be formed, the tolerances to which the parts of the container must be manufactured are less rigid. Furthermore, the materials from which the container of the invention may be manufactured (discussed below) are more easily and economically formed than those from which the containers of the prior art must be manufactured. Hence these containers are more economical to manufacture than those of the prior art, all other factors being equal.

Further, the capsule of the invention provides air venting means between the lower, silver-containing portion and the upper, mercury-containing portion, whereby a substantial portion of the excess air, which would have been compressed within the silver alloy containing chamber during the assembly of the capsule, is vented and allowed to escape into the atmosphere. These air venting means greatly decrease the amount of air compressed within the capsule during its assembly and thus greatly decrease the number of accidental disassemblies due to the heating of such trapped air. Any means for venting air from within the lower, silver alloy containing chamber while still allowing complete closure thereof when fully assembled is included within the scope of the present invention. Such means might be a channel or channels in the surface of a portion of the capsule, a hole or holes through a wall of a portion of the capsule, or the like.

IN THE FIGURES

FIG. 1 is a perspective of a preferred embodiment of the container of the invention;

FIG. 2 is a section taken along line 2—2 of FIG. 1 showing the container in its open mode;

FIG. 3 is an exploded section taken along line 3—3 of FIG. 2;

FIG. 4 is an exploded perspective of FIG. 1;

FIG. 5 is a view through line 5—5 of FIG. 3;

DETAILED DESCRIPTION OF THE FIGURES

Figure 6:
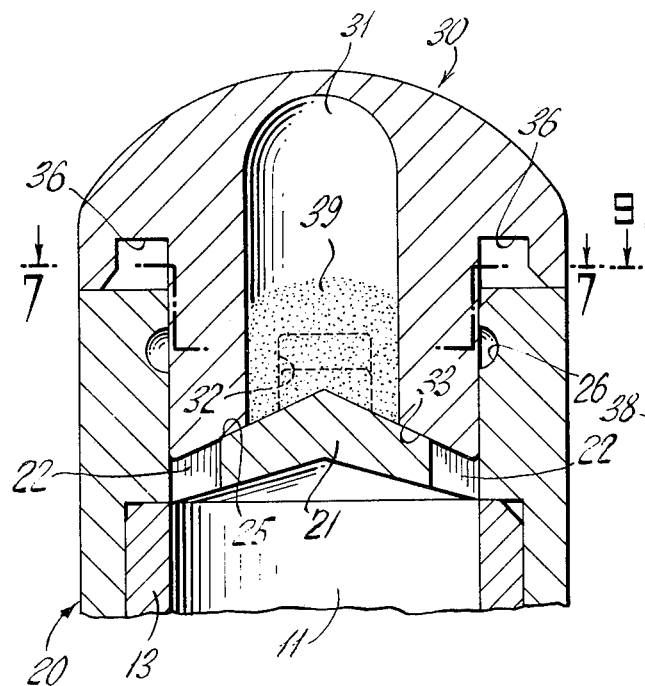
FIG. 6 is an enlarged view of the top portion of FIG. 2.

Referring now in greater detail to the drawings, the container of the invention comprises first portion 10, second portion 20, and third portion 30. The first portion is generally cylindrical and has chamber 11 therein for containing silver alloy 14. In this preferred embodiment, the first portion has knurling 12 about its circumference adjacent the closed end. Any suitable friction-producing gripping means may be used, but the crenelated form shown in FIGS. 1 and 4 is preferred because it makes for uniform wall thickness (and hence even cooling during manufacture) as well as ease of molding. The first portion also has indented wall 13 on its upper end adapted to frictionally engage indented wall 23 on the second portion.

The second portion is seen to be generally cylindrical and open at both ends, having barrier 21 spaced between the ends. Upper surface 25 of this barrier is convex to promote the flow of mercury from the third portion into the first portion through openings 22 in the barrier. Groove 26 in the interior of the upper end of the second portion is adapted to engage bead 34 on the third portion so as to rotatably attach them. Stops 24 are adapted to engage stop channels 36 on the third portion so as to stop rotation of the third portion with respect to the second portion at desired relationships to be defined below. On the interior surface of the second portion are channels 27 to allow for the egress of air from the interior of the silver alloy containing chamber when the second and third portions are engaged. These channels are slightly shorter than indented wall 13 on the first portion, so that when the two portions are completely engaged a tight seal is made between them. While these channels are shown as being on the interior surface of the second portion, they could also be on the exterior surface of indented wall 13 of the first portion.

The third portion has axially positioned chamber 31 for containing mercury 39 and conduit 32 communicating with the chamber. At the ends of conduit 32 there are webs 38 designed to prevent mercury from splashing out during filling of chamber 31 as discussed below. These webs obstruct only the upper portion of the conduit ends. Bottom surface 33 of the third portion is adapted slidably to engage top surface 25 of barrier 21 when bead 34 engages groove 26, so as to provide a liquid-tight seal between bottom surface 33 and top surface 25. Bead 34 may extend completely about the circumference of the third portion or (in the preferred embodiment) may comprise two separate opposed projections. Stop channels 36 and stops 24 are arranged so that clockwise rotation of the third portion with respect to the second portion (viewed from the top) is stopped when conduit 32 is juxtaposed to openings 22 and so that counter-clockwise rotation is stopped after a rotation of about 90° from the open position. Knurling 35 about the circumference of the third portion is provided to insure a firm grip thereon for rotational motion. Any suitable friction-producing gripping means may be used, but the crenelated form shown herein is preferred for the reasons given above.

Referring to FIGS. 5 and 6, details of stops 24 and stop channels 34 are shown.

Figure 8:
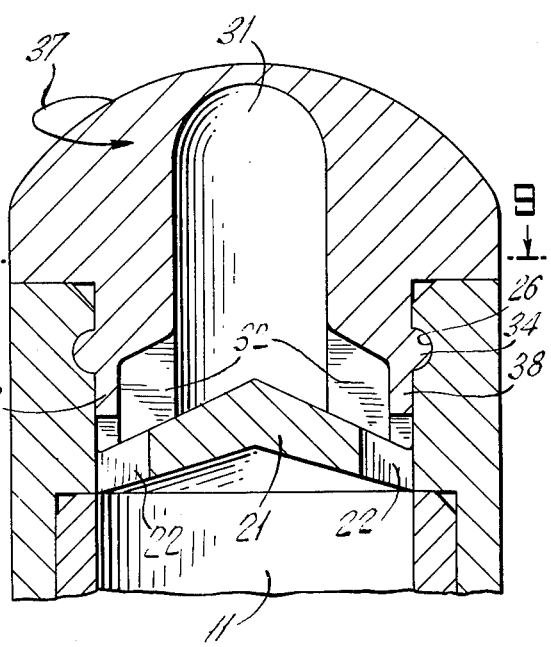
FIG. 8 is an enlarged view of the top portion of FIG. 2 in which the third portion of the container has been rotated 90° with respect to the lower two portions.

Referring to FIGS. 6 and 8, there are seen enlarged sections of the upper portion of the capsule through the same plane as in FIG. 2, but with the third portion rotated 90° in the direction of arrow 37 in FIG. 8 to open communication between chamber 31 and chamber 11 and to allow the mercury to flow from the former to the latter for mixing with the silver alloy.

Figure 7:
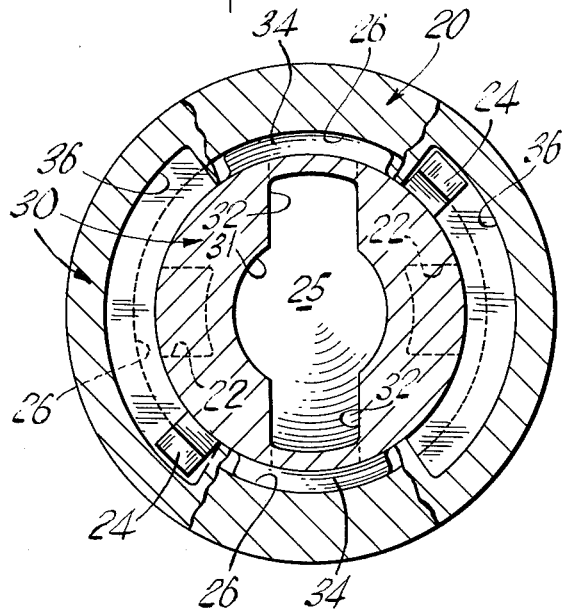
FIG. 7 is a section taken along line 7—7 of FIG. 6.
Figure 9:
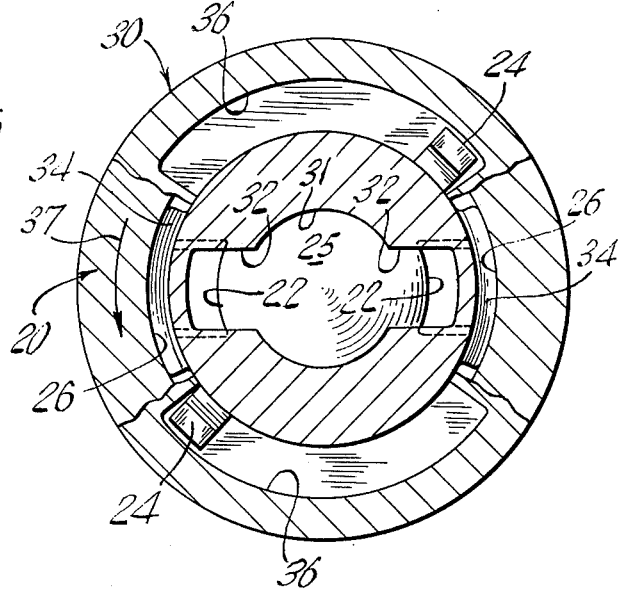
FIG. 9 is a section taken along line 9—9 of FIG. 8.

In the use of the container of the invention, a measured amount of silver alloy 14 is placed in chamber 11 of the first portion along with mixing pestle 15. The proper amount of mercury 39 to form dental amalgam with this amount of silver alloy is then placed in chamber 31 of the third portion, conveniently when it is positioned with the closed end downward. The third portion is then rotatably attached to the second portion and is rotated so as to close off openings 22 (FIGS. 2, 6, and 7). These two portions are then inverted and attached to the first portion. To prepare dental amalgam, the user holds the container in a generally vertical orientation with the third portion uppermost, rotates the third portion with respect to the two other portions to juxtapose conduits 32 with openings 22 and allow the mercury to flow from chamber 31 to chamber 11 (FIGS. 8 and 9), and then rotates the third portion back to its original position to close off openings 22. The container is then placed in an amalgamator or other similar device for effecting mixing of the ingredients and the mercury and silver alloy are mixed to form dental amalgam, after which the first portion is disengaged from the second portion and the amalgam is removed.

To realize the advantages of the container of the invention to their fullest extent, the first and third portions should be made of rigid material, such as metal, plastic, or the like. In the preferred embodiment they are made of a clear, rigid, thermoplastic material such as, for example, polystyrene, polycarbonate, polyacrylic, polyvinyl chloride, or the like. The material of choice is styrene acrylonitrile copolymer (SAN), manufactured and sold for example by Dow Chemical Company under the trade name "TYRIL."

The second portion should be made of a flexible material which is self-adjusting to slight differences in tolerance between the portions such as, for example, high-density polyethylene, polypropylene, nylon, or the like thermoplastic materials. The material of choice is high-density polyethylene.

The three portions are preferably formed by injection molding, but any suitable technique for forming the materials may be employed.

The use of a rigid material for the first portion and a flexible material for the second portion promotes the "wiping" action of the conduit edge over the barrier, as discussed above. Further, this combination requires less strict manufacturing tolerances for the portions because the flexible material of the second portion will adjust to minor deviations in the structure of the other portions, leading to more economic and efficient manufacture of the container of the invention. In those prior art devices employing a pulling action, on the other hand, the portions corresponding to the second and third portions of the container of the present invention must both be made of flexible materials. This requirement increases the cost of manufacture because flexible materials are more difficult to mold. Further, the joint between two flexible materials cause the large degree of friction discussed above as a severe disadvantage of this type of prior art container.

According to the invention, the premeasured ingredients can be mixed without being touched or measured by the user in a more accurate and simple fashion then previously known. It should be understood that while the container of the invention has been exemplified in the mixing of silver dental amalgam, other dental compositions such as acrylate polymer dental filling materials may be packaged and mixed therein. Further, the container may be used in fields other than dentistry where ingredients must be kept separate until just prior to use, as for example in the prepackaging of epoxy resins and accelerators for the formation of cements.

The scope of the present invention is not to be limited to the specific embodiment shown herein, which is for purposes of illustration only. Many modifications and deviations may be made therefrom without departing from the scope of the present invention, which scope is defined only in the appended claims.

What is claimed is:

1. A container for prepackaging materials which must be kept separate until just prior to use comprising:
   a. a generally cylindrical first portion having an open top end and a closed bottom end defining a chamber;
   b. a generally cylindrical second portion having an open top end, an open bottom end, an inner surface and valve means intermediate said ends, said second portion having its bottom end secured to the top end of said first portion;
   c. a third portion having a chamber therein and one end rotatably connected with the top end of said second portion, said third portion having valve closing means whereby said valve means on said second portion may be temporarily closed and the chambers in said first portion and said third portion temporarily separated from one another;
   d. air venting means whereby air may be vented from the chamber in said first portion during assembly of said capsule to prevent accidental disassembly thereof due to heating and consequent expansion of said air.

2. A container as in claim 1 wherein the top end of said first portion is secured to the bottom end of said second portion by frictional engagement of the former within the latter and wherein said air venting means comprise a channel in the interior surface of said second portion, said channel being substantially parallel to the axis of said cylindrical second portion, said channel communicating with the atmosphere when said first portion is partially engaged within said second portion, and the length of said channel being less than the length of said first portion which is frictionally engaged within said second portion.

3. A container as in claim 1 wherein said valve means comprises a barrier with a constricted opening therethrough adjacent the inner surface of said second portion, said barrier having a top surface; and wherein said valve closing means comprises sliding means on said one end of said third portion adapted to engage the top surface of said barrier and close said opening, means for rotatably connecting said one end with the top end of said second portion, and a conduit extending from said chamber through said sliding means so that rotation of said third portion with respect to said second portion causes said conduit to be aligned with said barrier opening to connect the chamber in said third portion with the chamber in said first portion.

4. A container as in claim 3 wherein the top end of said first portion is secured to the bottom end of said second portion by frictional engagement of the former within the latter and wherein said air venting means comprise a channel in the interior surface of said second portion, said channel being substantially parallel to the axis of said cylindrical second portion, said channel communicating with the atmosphere when said first portion is frictionally engaged within said second portion, and the length of said channel being less than the length of said first portion which is frictionally engaged within said second portion.

5. A container for prepackaging materials which must be kept separate until just prior to use comprising;
   a. a generally cylindrical first portion having an outer surface, an open top end, and a closed bottom end defining a chamber;
   b. a generally cylindrical second portion having an open top end, an open bottom end, an inner surface, and an outer surface and having a barrier spaced between said ends with a constricted opening therethrough adjacent said inner surface, said barrier having a top surface, and said second portion having its bottom end secured to the top end of said first portion; and
   c. a third portion having an axially positioned chamber therein and one end having sliding means adapted to engage the top surface of said barrier in said second portion and close said opening and means for rotatably connecting said one end with the top end of second portion, said third portion also having a conduit extending from said chamber through said sliding means so that rotation of said third portion with respect to said second portion causes said conduit of said third portion to be aligned with said opening in the barrier of said second portion to connect said chamber in said third portion with the chamber in said first portion.

6. A container as in claim 5 wherein said first portion and said third portion are made of a clear, rigid, thermoplastic material and wherein said second portion is made of a flexible, thermoplastic material which is self-adjusting to slight differences in tolerance between said second portion and said first and said third portions.

7. A container as in claim 5 wherein said second portion and said third portion have means for limiting the extent of rotation of said third portion with respect to said second portion.

8. A container as in claim 5 wherein there is a quantity of mercury in the chamber of said third portion and a quantity of silver alloy and a mixing pestle in the chamber of said first portion.

9. A container as in claim 5 wherein said first portion and said third portion are made of styrene-acrylonitrile copolymer and wherein said second portion is made of high-density polyethylene.

10. A container as in claim 5 wherein there are friction-producing gripping means about the circumference of said first portion and about the circumference of said third portion.

11. A container as in claim 5 wherein the top surface of the barrier in said second portion is convex, to promote complete transfer of fluid material from the chamber of said third portion to the chamber of said first portion when the conduit in said third portion is aligned with the opening in said barrier.

* * * * *